US008821458B2

(12) United States Patent
Locke et al.

(10) Patent No.: US 8,821,458 B2
(45) Date of Patent: Sep. 2, 2014

(54) EVAPORATIVE BODY-FLUID CONTAINERS AND METHODS

(75) Inventors: Christopher Brian Locke, Bournemouth (GB); Aidan Marcus Tout, Alderbury (GB); Timothy Mark Robinson, Basingstoke (GB)

(73) Assignee: KCI Licensing, Inc., San Antonio, TX (US)

( * ) Notice: Subject to any disclaimer, the term of this patent is extended or adjusted under 35 U.S.C. 154(b) by 93 days.

(21) Appl. No.: 13/084,758

(22) Filed: Apr. 12, 2011

(65) Prior Publication Data

US 2011/0257613 A1 Oct. 20, 2011

Related U.S. Application Data

(60) Provisional application No. 61/359,205, filed on Jun. 28, 2010, provisional application No. 61/325,115, filed on Apr. 16, 2010, provisional application No. 61/359,181, filed on Jun. 28, 2010.

(51) Int. Cl.
*A61M 1/00* (2006.01)
*A61F 13/02* (2006.01)
*A61F 13/00* (2006.01)

(52) U.S. Cl.
CPC ........... *A61M 1/0088* (2013.01); *A61M 1/0052* (2014.02); *A61M 2205/7527* (2013.01); *A61M 1/009* (2014.02); *A61M 2205/7536* (2013.01); *A61M 1/0066* (2013.01); *A61M 1/0031* (2013.01); *A61M 1/0001* (2013.01); *A61M 1/0058* (2013.01); *A61F 13/02* (2013.01); *A61F 2013/0074* (2013.01); *A61F 2013/00536* (2013.01)
USPC ........................................................ 604/319

(58) Field of Classification Search
USPC ........................................................ 604/319
See application file for complete search history.

(56) References Cited

U.S. PATENT DOCUMENTS

| 1,355,846 A | 10/1920 | Rannells |
| 2,547,758 A | 4/1951 | Keeling |
| 2,632,443 A | 3/1953 | Lesher |

(Continued)

FOREIGN PATENT DOCUMENTS

| AU | 550575 A1 | 8/1982 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (certified translation).

(Continued)

*Primary Examiner* — Susan Su
*Assistant Examiner* — Guy K Townsend

(57) ABSTRACT

Body-fluid containers, methods, and systems are presented that include a container that has a container housing formed, at least in part, by a liquid-impermeable, vapor-permeable material. The liquid-impermeable, vapor-permeable material allows water to evaporate and be transmitted outside of the container. The evaporation allows more fluid to be processed by the container than the container could otherwise hold. Other systems, methods, and apparatuses are presented.

25 Claims, 13 Drawing Sheets

(56) References Cited

U.S. PATENT DOCUMENTS

| | | | |
|---|---|---|---|
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,565,635 A * | 1/1986 | Le Du et al. | 210/727 |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,061,258 A * | 10/1991 | Martz | 604/307 |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,284,621 A | 2/1994 | Kaufman | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,591,790 A * | 1/1997 | Lock | 524/35 |
| 5,593,395 A * | 1/1997 | Martz | 604/304 |
| 5,607,388 A | 3/1997 | Ewall | |
| 5,636,643 A | 6/1997 | Argenta et al. | |
| 5,645,081 A | 7/1997 | Argenta et al. | |
| 5,986,163 A * | 11/1999 | Augustine | 602/42 |
| 6,071,254 A * | 6/2000 | Augustine | 602/2 |
| 6,071,267 A | 6/2000 | Zamierowski | |
| 6,135,116 A | 10/2000 | Vogel et al. | |
| 6,213,966 B1 * | 4/2001 | Augustine | 602/2 |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,419,651 B1 * | 7/2002 | Augustine | 602/2 |
| 6,420,622 B1 * | 7/2002 | Johnston et al. | 602/41 |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,566,575 B1 * | 5/2003 | Stickels et al. | 602/41 |
| 6,814,079 B2 | 11/2004 | Heaton et al. | |
| 6,840,915 B2 * | 1/2005 | Augustine | 602/2 |
| 7,108,683 B2 * | 9/2006 | Zamierowski | 604/304 |
| 7,198,046 B1 * | 4/2007 | Argenta et al. | 128/897 |
| 7,216,651 B2 * | 5/2007 | Argenta et al. | 128/897 |
| 7,438,705 B2 * | 10/2008 | Karpowicz et al. | 604/313 |
| 7,477,939 B2 * | 1/2009 | Sun et al. | 604/20 |
| 7,615,036 B2 * | 11/2009 | Joshi et al. | 604/313 |
| 7,772,455 B1 * | 8/2010 | Roe et al. | 604/360 |
| 7,909,805 B2 * | 3/2011 | Weston | 604/313 |
| 8,062,272 B2 * | 11/2011 | Weston | 604/313 |
| 8,177,763 B2 * | 5/2012 | Wiesner | 604/313 |
| 8,409,160 B2 * | 4/2013 | Locke et al. | 604/319 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0128578 A1 * | 9/2002 | Johnston et al. | 602/43 |
| 2002/0143286 A1 | 10/2002 | Tumey | |
| 2002/0183676 A1 * | 12/2002 | Augustine | 602/42 |
| 2003/0040687 A1 * | 2/2003 | Boynton et al. | 601/6 |
| 2003/0050594 A1 * | 3/2003 | Zamierowski | 604/46 |
| 2003/0144619 A1 * | 7/2003 | Augustine | 602/2 |
| 2004/0006319 A1 * | 1/2004 | Lina et al. | 604/304 |
| 2005/0077225 A1 * | 4/2005 | Usher et al. | 210/321.6 |
| 2005/0222544 A1 * | 10/2005 | Weston | 604/313 |
| 2005/0261642 A1 * | 11/2005 | Weston | 604/313 |
| 2006/0020235 A1 | 1/2006 | Siniaguine | 602/41 |
| 2007/0016152 A1 * | 1/2007 | Karpowicz et al. | 604/326 |
| 2007/0038172 A1 * | 2/2007 | Zamierowski | 604/20 |
| 2007/0129707 A1 * | 6/2007 | Blott et al. | 604/543 |
| 2007/0141128 A1 * | 6/2007 | Blott et al. | 424/445 |
| 2007/0167926 A1 * | 7/2007 | Blott et al. | 604/304 |
| 2007/0219513 A1 * | 9/2007 | Lina et al. | 604/304 |
| 2007/0219532 A1 * | 9/2007 | Karpowicz et al. | 604/540 |
| 2007/0265585 A1 * | 11/2007 | Joshi et al. | 604/313 |
| 2007/0265586 A1 * | 11/2007 | Joshi et al. | 604/313 |
| 2008/0082059 A1 * | 4/2008 | Fink et al. | 604/305 |
| 2008/0167594 A1 * | 7/2008 | Siniaguine | 602/48 |
| 2008/0171726 A1 * | 7/2008 | Roth et al. | 514/144 |
| 2009/0124988 A1 * | 5/2009 | Coulthard | 604/313 |
| 2009/0221990 A1 | 9/2009 | Jaeb et al. | |
| 2009/0227969 A1 | 9/2009 | Jaeb et al. | |
| 2009/0240218 A1 * | 9/2009 | Braga et al. | 604/313 |
| 2009/0275905 A1 | 11/2009 | Clementi et al. | |
| 2009/0292263 A1 | 11/2009 | Hudspeth et al. | |
| 2010/0063463 A1 | 3/2010 | Wiesner | |
| 2011/0054423 A1 * | 3/2011 | Blott et al. | 604/319 |
| 2011/0257613 A1 * | 10/2011 | Locke et al. | 604/319 |

(56) References Cited

U.S. PATENT DOCUMENTS

FOREIGN PATENT DOCUMENTS

| AU | 755496 | | 2/2002 |
|---|---|---|---|
| CA | 2005436 | | 6/1990 |
| DE | 26 40 413 | A1 | 3/1978 |
| DE | 43 06 478 | A1 | 9/1994 |
| DE | 295 04 378 | U1 | 10/1995 |
| EP | 0100148 | A1 | 2/1984 |
| EP | 0117632 | A2 | 9/1984 |
| EP | 0161865 | A2 | 11/1985 |
| EP | 0358302 | A2 | 3/1990 |
| EP | 1018967 | B1 | 8/2004 |
| EP | 1905465 | A1 | 4/2008 |
| GB | 692578 | | 6/1953 |
| GB | 2 195 255 | A | 4/1988 |
| GB | 2 197 789 | A | 6/1988 |
| GB | 2 220 357 | A | 1/1990 |
| GB | 2 235 877 | A | 3/1991 |
| GB | 2 333 965 | A | 8/1999 |
| GB | 2 329 127 | B | 8/2000 |
| JP | 4129536 | | 4/1992 |
| SG | 71559 | | 4/2002 |
| WO | WO 80/02182 | | 10/1980 |
| WO | WO 87/04626 | | 8/1987 |
| WO | WO 90/10424 | | 9/1990 |
| WO | WO 93/09727 | | 5/1993 |
| WO | WO 94/20041 | | 9/1994 |
| WO | WO 96/05873 | | 2/1996 |
| WO | WO 97/18007 | | 5/1997 |
| WO | WO 99/13793 | | 3/1999 |
| WO | 2009004370 | A1 | 1/2009 |
| WO | WO 2009/004370 | A1 | 1/2009 |
| WO | WO 2009/066105 | A1 | 5/2009 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.
Susan Mendez-Eastman, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinović, V. Ð ukić, Ž. Maksimović, Ð . Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schrnieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211, (1909).
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference

(56) References Cited

OTHER PUBLICATIONS on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

International Search Report and Written Opinion date mailed Aug. 29, 2011; PCT International Patent Application No. PCT/US2011/032547.

Extended European Search Report for EP Application No. 13181569.8, Dated Mar. 12, 2013.

* cited by examiner

EVAPORATIVE BODY-FLUID CONTAINERS AND METHODS

RELATED APPLICATION

The present invention claims the benefit, under 35 USC §119(e), of the filing of U.S. Provisional Patent Application Ser. No. 61/359,205, entitled "Evaporative Body Fluid Containers and Methods," filed 28 Jun. 2010, which is incorporated herein by reference for all purposes; U.S. Provisional Patent Application Ser. No. 61/325,115, entitled "Reduced-Pressure Sources, Systems, and Methods Employing A Polymeric, Porous, Hydrophobic Material," filed 16 Apr. 2010, which is incorporated herein by reference for all purposes; and U.S. Provisional Patent Application Ser. No. 61/359,181, entitled "Dressings and Methods For Treating a Tissue Site On A Patient," filed 28 Jun. 2010, which is incorporated herein by reference for all purposes.

BACKGROUND

The present disclosure relates generally to medical treatment systems and, more particularly, but not by way of limitation, to evaporative body fluid containers, systems, dressings, and methods. The evaporative body fluid containers, systems, dressings, and methods may be used with reduced-pressure treatment systems.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, reduced pressure is applied to tissue through a porous pad or other manifold device. The porous pad contains cells or pores that are capable of distributing reduced pressure to the tissue and channeling fluids that are drawn from the tissue. As the reduced pressure is applied, body fluids, e.g., exudates, are received and typically contained in a reservoir.

SUMMARY

According to one illustrative embodiment, a system for treating a tissue site on a patient includes a treatment manifold for placing proximate to the tissue site, and a sealing member for forming a fluid seal over the treatment manifold and a portion of the patient's epidermis. The sealing member is for forming a sealed treatment space over the tissue site, wherein the sealed treatment space receives fluids. The system further includes a reduced-pressure source for providing reduced pressure and a container fluidly coupled to the reduced-pressure source and to the sealed treatment space for receiving fluids. The container includes a container housing having an interior space for receiving the fluids and a fluid inlet through the container housing. The fluid inlet is for receiving the fluids into the interior space of the container housing. At least a portion of the container housing includes a liquid-impermeable, vapor-permeable material that allows egress of evaporated liquids from the fluids.

According to another illustrative embodiment, a container for receiving and processing body fluids (primarily liquids) includes a container housing having an interior space for receiving the body fluids and a body fluid inlet through the container housing. The body fluid inlet is for receiving body fluids into the interior space of the container housing. At least a portion of the container housing comprises a liquid-impermeable, vapor-permeable material.

According to another illustrative embodiment, a method for removing and processing body fluids from a patient includes removing the body fluids from the patient and causing the body fluids to enter into a container. The container includes container housing having an interior space for receiving the body fluids and a body fluid inlet through the container housing. The body fluid inlet is for receiving body fluids into the interior space of the container housing. At least a portion of the container housing includes a liquid-impermeable, vapor-permeable material. The method further includes evaporating and removing at least a portion of the body fluids using the liquid-impermeable, vapor-permeable material.

According to another illustrative embodiment, a wound dressing for treating a wound on a patient includes an absorbent layer having a first side and a second, patient-facing side. The absorbent layer is in fluid communication with the wound. The wound dressing also includes a liquid-impermeable, vapor-permeable layer covering the absorbent layer and the wound. The liquid-impermeable, gas-impermeable layer is operable to allow body fluids from the absorbent layer to evaporate and exit the liquid-impermeable, gas-impermeable layer.

According to another illustrative embodiment, a method of manufacturing a container for receiving body fluids includes forming a container housing having an interior space for receiving the body fluids and forming a body fluid inlet on the container housing. The body fluid inlet is for receiving body fluids into the interior space of the container housing. At least a portion of the container housing includes a liquid-impermeable, vapor-permeable material that allows evaporated body fluids (vapor) to egress the interior space.

Other features and advantages of the illustrative embodiments will become apparent with reference to the drawings and detailed description that follow.

DETAILED DESCRIPTION OF ILLUSTRATIVE EMBODIMENTS

In the following detailed description of the illustrative embodiments, reference is made to the accompanying drawings that form a part hereof These embodiments are described in sufficient detail to enable those skilled in the art to practice the inventions, and it is understood that other embodiments may be utilized and that logical structural, mechanical, electrical, and chemical changes may be made without departing from the spirit or scope of the inventions. To avoid detail not necessary to enable those skilled in the art to practice the embodiments described herein, the description may omit certain information known to those skilled in the art. The following detailed description is not to be taken in a limiting sense, and the scope of the illustrative embodiments is defined only by the appended claims.

Figure 1:
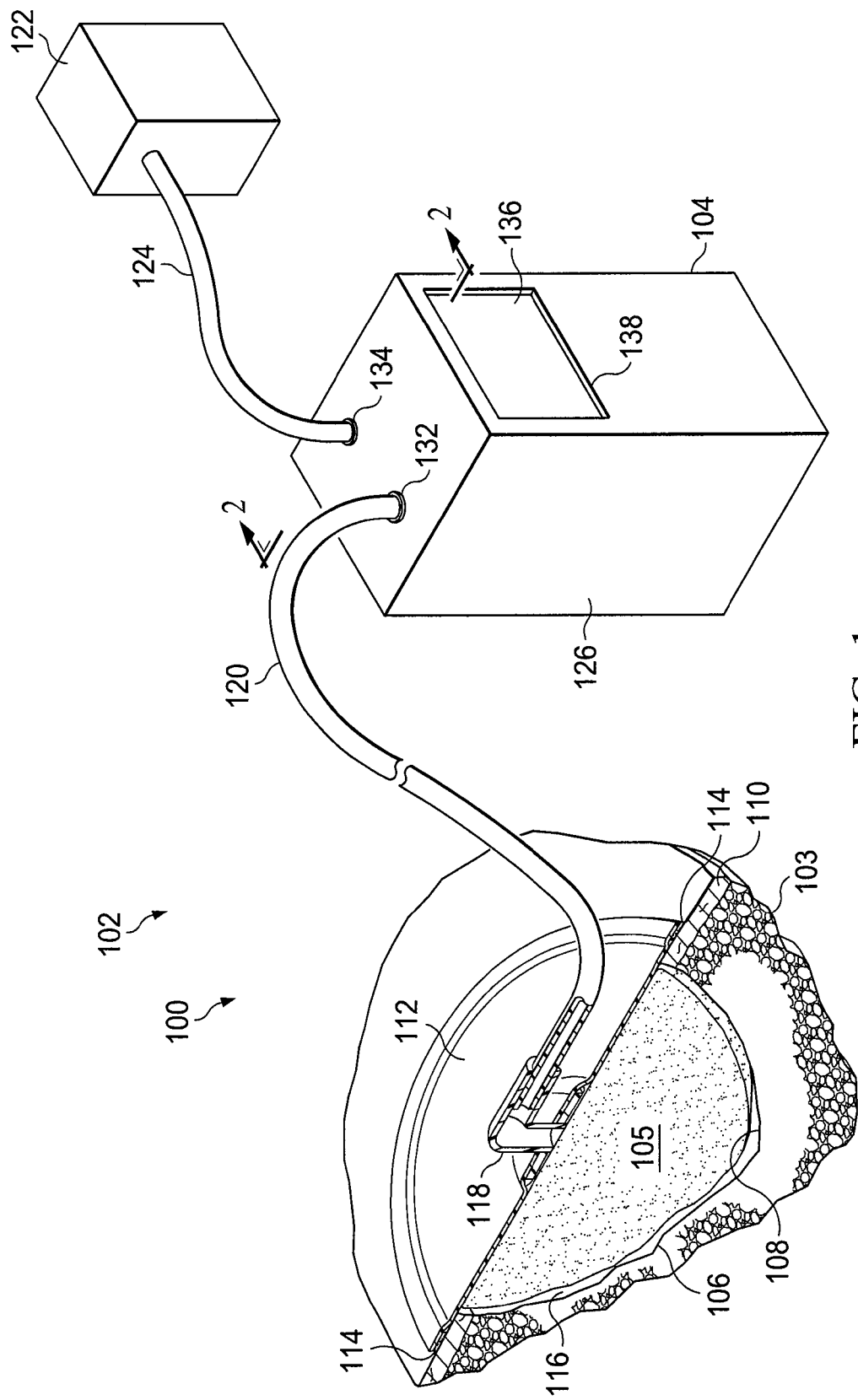
FIG. 1 is a schematic, perspective view of an illustrative, non-limiting medical treatment system that includes an illustrative embodiment of a container for receiving and processing body fluids.
Figure 2:
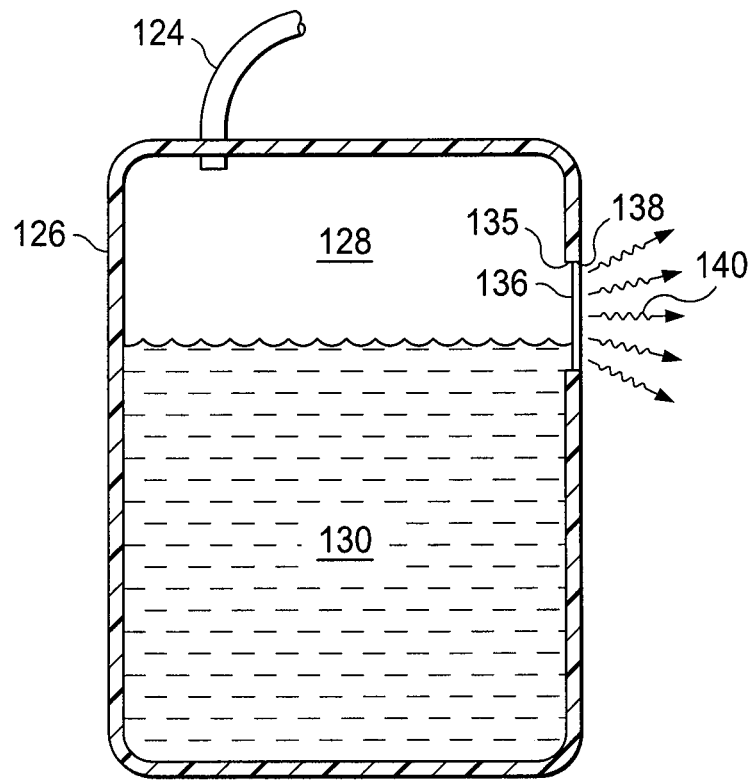
FIG. 2 is a schematic cross section of the illustrative container for receiving and processing body fluids of FIG. 1.

Referring to the drawings and primarily to FIGS. 1-2, an illustrative embodiment of a medical treatment system 100, such as a reduced-pressure treatment system 102, is presented. The reduced-pressure treatment system 102 includes an illustrative embodiment of a container 104 for receiving and processing body fluids (primarily liquids) from a patient 103. The container 104 is operable to process more liquids over time than the container 104 can physically retain at one time.

The reduced-pressure treatment system 102 may include a treatment manifold 105 that is placed proximate to a tissue site 106, such as a wound 108. The wound 108 is shown through the patient's epidermis 110. The tissue site 106 may be the bodily tissue of any human, animal, or other organism, including bone tissue, adipose tissue, muscle tissue, dermal tissue, vascular tissue, connective tissue, cartilage, tendons, ligaments, or any other tissue.

The treatment manifold 105 and a portion of the patient's epidermis 110 may be covered by a sealing member 112 to form a sealed treatment space 116. The sealing member 112 may be any material that provides a fluid seal. The sealing member 112 maybe, for example, an impermeable or semi-permeable, elastomeric material. "Elastomeric" means having the properties of an elastomer. Elastomeric generally refers to a polymeric material that has rubber-like properties. More specifically, most elastomers have ultimate elongations greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Additional specific examples of sealing members 112 include a silicone drape, 3M Tegaderm® drape, PU drape, such as one available from Avery Dennison Corporation of Pasadena, Calif.

An attachment device 114 may be used with the sealing member 112 to form a fluid seal over the wound 108 and the treatment manifold 105. The attachment device 114 may take numerous forms. For example, the attachment device 114 may be a medically acceptable, pressure-sensitive adhesive or a hydrocolloid material that extends about a periphery of the sealing member 112. The sealing member 112 forms the sealed treatment space 116 in which the treatment manifold 105 is disposed. Reduced pressure is supplied to the sealed treatment space 116, and body fluids 130 are thereby removed from the sealed treatment space 116.

A reduced-pressure interface 118 may be used to fluidly couple a first reduced-pressure delivery conduit 120 to the sealed treatment space 116. In one illustrative embodiment, the reduced-pressure interface 118 is a T.R.A.C.® Pad or Sensa T.R.A.C.® Pad available from KCI of San Antonio, Tex. Other devices may be used for the reduced-pressure interface 118 provided that the reduced pressure is delivered to the sealed treatment space 116.

The first reduced-pressure delivery conduit 120 is fluidly coupled to the container 104 and delivers the body fluids 130 to the container 104. The container 104 receives reduced pressure from a reduced-pressure source 122 via a second reduced-pressure delivery conduit 124. The reduced-pressure source 122 may be any device for supplying a reduced pressure, such as a vacuum pump, wall suction, or other source. While the amount and nature of reduced pressure applied to a tissue site will typically vary according to the application, the reduced pressure will typically be between −5 mm Hg (−667 Pa) and −500 mm Hg (−66.7 kPa) and more typically between −75 mm Hg (−9.9 kPa) and −300 mm Hg (−39.9 kPa). For example, and not by way of limitation, the pressure may be −12, −12.5, −13, −14, −14.5, −15, −15.5, −16, −16.5, −17, −17.5, −18, −18.5, −19, −19.5, −20, −20.5, −21, −21.5, −22, −22.5, −23, −23.5, −24, −24.5, −25, −25.5, −26, −26.5 kPa or another pressure.

The container 104 receives the body fluids 130. The body fluids 130 are removed from the body by the reduced-pressure treatment system 102. For example, exudates, ascites, or other body fluids are usually removed and placed in the container 104. Many body fluids, e.g., exudates, are substantially water based. The exudates in a fluid reservoir, without an additive, will not typically change state to a solid or gel, but in the present embodiment may change to a gel state as water is removed through a liquid-impermeable, vapor-permeable material 136.

The container 104 may be rigid, semi-rigid, or flexible. The container 104 includes a container housing 126 having an interior space 128 for receiving the body fluids 130. The container housing 126 has a body fluid inlet 132 for receiving the body fluids 130 and a reduced pressure inlet 134 for receiving reduced pressure. In some embodiments that include a multi-lumen conduit (a lumen for reduced pressure supply and one for body fluids), the reduced-pressure inlet 134 may be the same as the body fluid inlet 132. At least a portion of the container housing 126 is formed from the liquid-impermeable, vapor-permeable material 136. In the illustrative embodiment of FIGS. 1-2, the portion of the container housing 126 with the liquid-impermeable, vapor-permeable material 136 is a window 138, but numerous locations are possible. The window 138 may be formed by forming at least one window aperture 135 and covering the window-aperture with the liquid-impermeable, vapor-permeable material 136. The container housing 126 may be formed with any stiffness, e.g., rigid, flexible, semi-rigid, etc.

The liquid-impermeable, vapor-permeable material 136 may form the whole container 104, or fluid reservoir, or may form only a portion, e.g., a wall or window 138. Typically, a higher evaporation can be obtained by having liquids within the container 104 in direct contact with the liquid-impermeable, vapor-permeable material 136.

Figure 6:
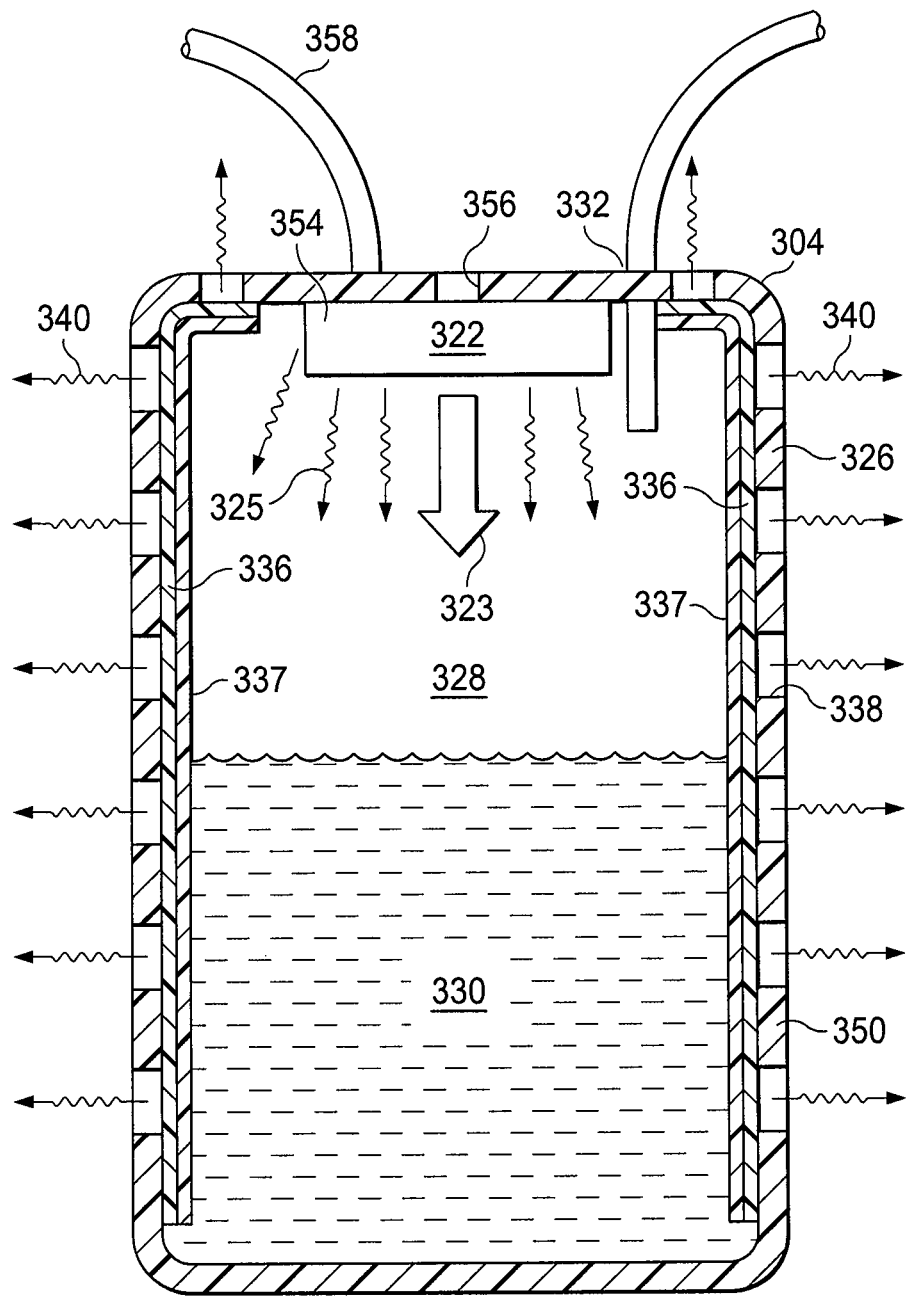
FIG. 6 is a schematic cross section of the container of FIG. 5.

In addition to having the liquid contact the liquid-impermeable, vapor-permeable material 136, a higher evaporation rate may be achieved by adding thermal energy to the body fluids 130, increasing air flow across the exterior of the liquid-impermeable, vapor-permeable material 136 (see FIGS. 10-11), or otherwise adding energy to the body fluids or air inside the container. The thermal energy may be added by delivering thermal energy from a vacuum pump for the reduced-pressure treatment system to the body fluids 130. For example, as shown in FIG. 6, if a piezoelectric pump 354 is used, the piezoelectric pump 354 may be disposed in a container 304 so that any heat developed by the piezoelectric pump 354 is delivered to the body fluids 330 therein. In another illustrative embodiment, a dedicated heating element (not shown), e.g., a resistor element, may be added to the interior space 128 of the container 104. In still another illustrative embodiment, an agitator (not shown) may be added to move the body fluids 130 against the liquid-impermeable, vapor-permeable material 136 to facilitate evaporation and transmission. In another illustrative embodiment, the air flow on an exterior of the liquid-impermeable, vapor-permeable material 136 may be increased, such as by a fan or other ventilation subsystem, to increase the evaporation rate. In another illustrative embodiment, the container 104 is placed adjacent to the patient's epidermis 110 to use thermal energy from the patient 103 to promote enhanced evaporation. In another illustrative embodiment, a chemical may be added to the interior space 128 to cause an exothermic reaction when mixed with exudates.

The liquid-impermeable, vapor-permeable material 136 material allows water vapor to exit or egress as suggested by arrows 140 (FIG. 2) while retaining liquids. At the same time, the liquid-impermeable, vapor-permeable material 136 allows a reduced pressure to be maintained within the container 104. The liquid-impermeable, vapor-permeable material 136 comprises any material that is capable of preventing liquids from ingress or egress through the material and yet is operable to permit vapor, e.g., evaporated water from the body fluids, to egress or to be transmitted through the material. Non-limiting, illustrative examples of the liquid-impermeable, vapor-permeable material 136 include a high moisture vapor transmission rate (MVTR) films or other structures formed from hydrophilic polymers. Illustrative materials may include polyvinyl alcohol, polyvinyl acetate, cellulose based materials (ethers, esters, nitrates, etc.), polyvinyl pyrrolidone, polyurethanes, polyamides, polyesters, polyacrylates and polymethacrylates, polyacrylamides. The materials for the liquid-impermeable, vapor-permeable material 136 may be crosslinked, blended, grafted, or copolymerized with each other.

In some embodiments, the materials for forming the liquid-impermeable, vapor permeable material may be surface treated to enhance hydrophylicity. The surface treatments may include chemical, plasma, light (UV), corona, or other ionizing radiation. In some embodiments, the material for forming the liquid-impermeable, vapor permeable material may be formed by forming (casting) films and crosslinking some of the natural gums, such as guar, xanthan and alginates, or gelatin. The materials used for the liquid-impermeable, vapor permeable material typically also serve as a bacteria barrier. While the material for forming the liquid-impermeable, vapor permeable materials herein is fairly impervious to nitrogen and oxygen, the material is pervious to water vapor. One specific, non-limiting example of a suitable material is a 15 micron sheet of Hytrel APA60015 from E. I. du Pont de Nemours and Company of Wilmington, Del., U.S.A.

Practical issues, e.g., odor and condensation, related to the container 104 may be addressed in a number of ways. First, with respect to any potential odor, a charcoal filter or a silver impregnated mesh may be used as part of the fluid path, e.g., in the first reduced-pressure delivery conduit 120 or body fluid inlet 132, to kill bacteria and to address the aroma of the vapor exiting the container 104. The risk of condensate on the container 104 may be reduced by managing the evaporation rate and by the design of the container 104 to ensure that there are no mechanical surfaces adjoining the evaporation surface that can be at a different temperature than the body fluids 130.

According to one illustrative embodiment, in operation, the treatment manifold 105 is disposed proximate to the tissue site 106. The sealing member 112 is placed over the treatment manifold 105 and a portion of the patient's epidermis 110 to form the sealed treatment space 116. If not already installed, the reduced-pressure interface 118 is installed on the sealing member 112 and the first reduced-pressure delivery conduit 120 is fluidly coupled to the reduced-pressure interface 118 and the body-fluid inlet 132 of the container 104. The second reduced-pressure delivery conduit 124 is fluidly coupled to the container 104 and the reduced-pressure source 122.

The reduced-pressure source 122 is activated. Reduced pressure is delivered to the tissue site 106 and the body fluids 130 are removed from the tissue site 106. The body fluids 130 are delivered through the body-fluid inlet 132 into the interior space 128 of the container 104. The water content of the body fluids 130 evaporates, at least in part, over an elapsed time period and is transmitted through the liquid-impermeable, vapor-permeable material 136.

As the liquids—typically water—in the body fluids 130 evaporate, a desiccated slurry results in the container 104 that contains non-water based products and other substances, such as proteins, fats, or salts (e.g., sodium, calcium, and chloride). The desiccated slurry will typically congeal and change state to be a solid or gel. Thus, the desiccated slurry may gel without an isolyzer. In some embodiments, an isolyzer may be added nonetheless.

Varying degrees of water may evaporate from the body fluids 130 depending on, among other things, the time allowed, temperature, and pressure. In some instances, greater than 5% of the water in the container 104 may evaporate. In other instances, greater than 10%, 20%, 30%, 40%, 50%, 60%, 70%, 80%, 90% or even more of the water in the container 104 may evaporate. The implicit ranges include all numbers in between.

The embodiment of the container 104 allows a smaller fluid reservoir because the container 104 is capable of processing more fluid volume ($V_f$) than the physical volume ($V_c$) of the container 104, i.e., operatively $V_f > V_c$. In some embodiments, the following relationships hold: $V_f > 105\% V_c$; $V_f > 110\% V_c$; $V_f > 120\% V_c$; $V_f > 130\% V_c$; $V_f > 150\% V_c$; or $V_f > 200\% V_c$. Other ratios are possible. As one illustrative, non-limiting example, the container 104 may hold 500 ml ($V_c$=500 ml), but over three days of use may receive 600-1000 ml of fluid ($V_f$=600 to 1000 ml). The smaller size reduces the cost of the container 104 for the reduced-pressure treatment system 102 or other system requiring body fluid collection. Because a smaller container may be used with a given medical treatment system, less polymer use is necessary and the cost of the reduced-pressure treatment system 102 may be reduced. The smaller container 104 is also typically more convenient for the patient. If the same size container is used, it will need changing less frequently than it otherwise would. The less frequent changes present a cost savings with respect to the patient's care.

The evaporative process within the container 104 may produce a reduced pressure itself. Thus, when the container 104 is used as part of a reduced-pressure treatment system 102, the resultant reduced pressure from the evaporative process augments the reduced pressure supplied by the reduced-pressure source 122 or potentially may make redundant the reduced-pressure source 122. In addition, in the present, illustrative embodiment, the body fluids 130 received into the container 104 may increase in density sufficiently to not require an isolyzer. Alternatively, a relatively reduced amount of isolyzer may be used.

Figure 3:
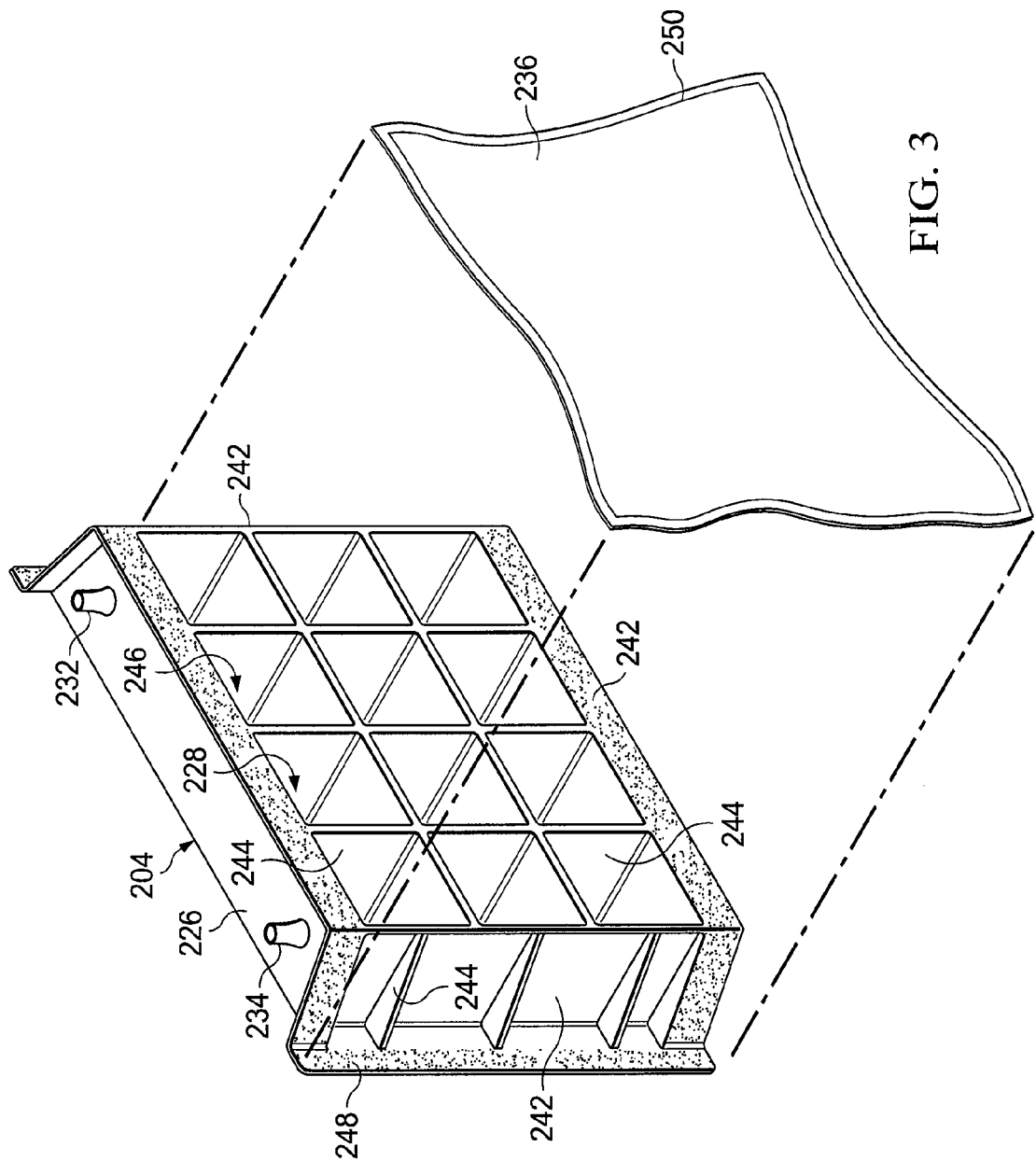
FIG. 3 is a schematic, perspective view, with a portion exploded, of an illustrative embodiment of a container for receiving and processing body fluids.
Figure 4:
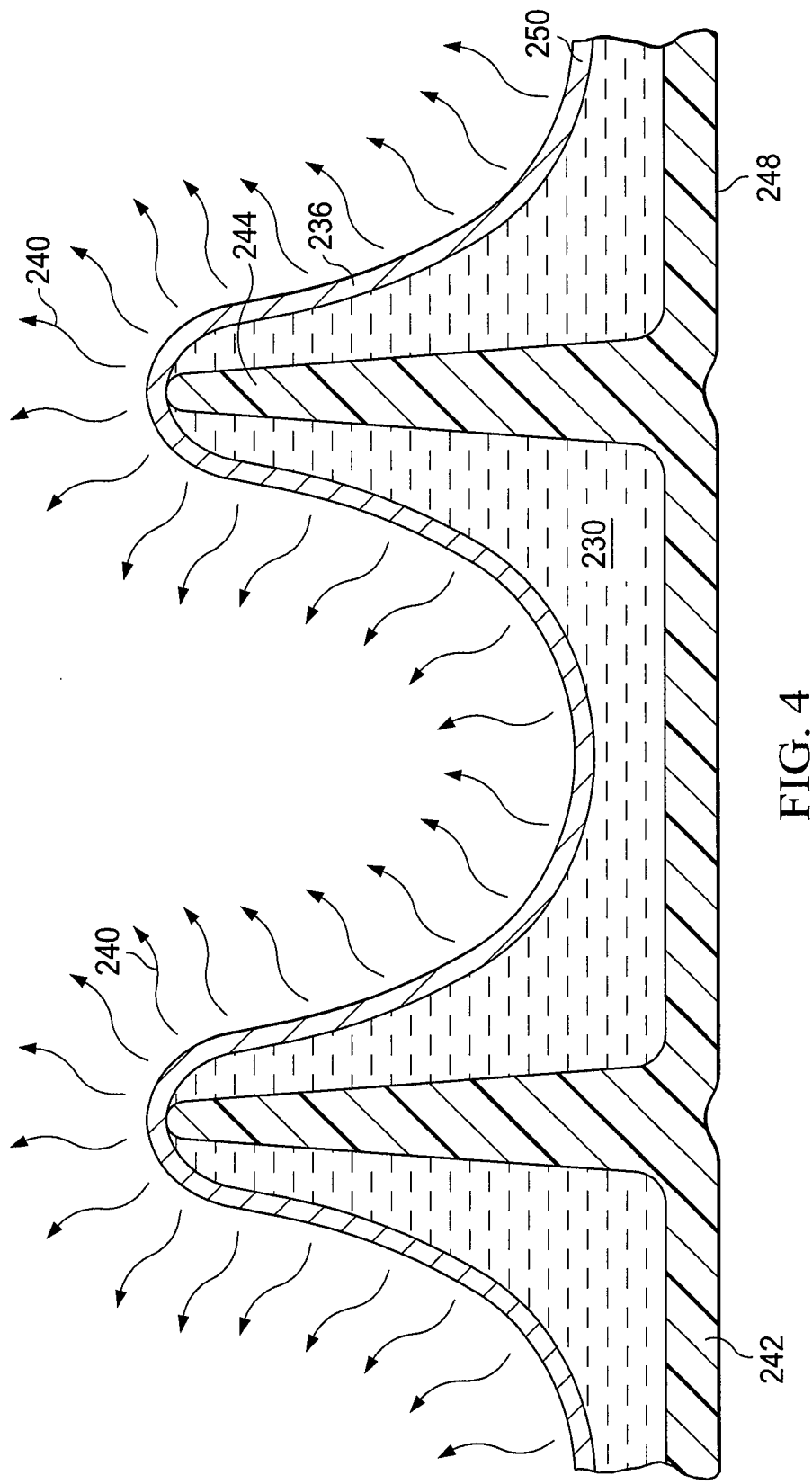
FIG. 4 is a schematic cross section of a portion of the container of FIG. 3 during operation.

Referring now primarily to FIGS. 3 and 4, another illustrative embodiment of a container 204 for receiving and processing body fluids 230 is presented. The container 204 may be used as part of a medical treatment system, such as the system 100 of FIG. 1. The container 204 includes a container housing 226 having an interior space 228 for receiving the body fluids 230. The container housing 226 may be formed from a container frame 242 and a plurality of baffles 244. The baffles 244 help form a plurality of waffle pockets 246, which are small compartments that are interconnected by apertures (not shown) in the baffles 244. (In another embodiment, the waffle pockets may be fluidly coupled by a common area, such as an open space above (for orientation with gravity) the waffle pockets). A liquid-impermeable, vapor-permeable material 236 is coupled to the container frame 242, such as by a weld 250 on a flange portion 248 of the frame member, or container frame 242. The liquid-impermeable, vapor-permeable material 236 may also be coupled to the ends of baffles 244 between the waffle pockets 246 in some embodiments. The baffles 244 may be uniform as shown or be at different dimensions to create more surface area for the liquid-impermeable, vapor-permeable material 236.

A body fluid inlet 232 may be formed on the container housing 226. The body fluid inlet 232 is for receiving the body fluids 230 into the interior space 228 of the container housing 226. A reduced pressure inlet 234 may also be formed in the container housing 226 to allow reduced pressure into the interior space 228. In another illustrative embodiment, reduced pressure may be omitted and the body fluids delivered with positive pressure. In such an embodiment, a vent opening (not shown) may be added.

As shown in FIG. 4, the waffle pockets 246 help increase the surface area of the liquid-impermeable, vapor-permeable material 236 that the body fluids 230 contacts. The increased surface area may enhance evaporation and vapor transmission of liquids from the body fluids 230. The vapor exiting the container 204 is suggested by arrows 240.

Figure 5:
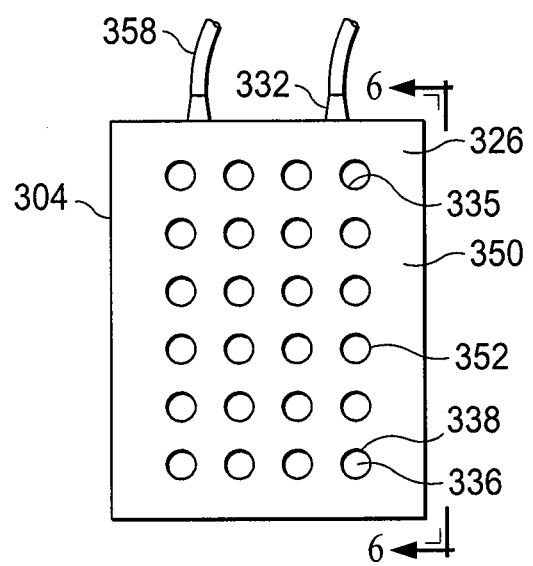
FIG. 5 is a schematic, front elevational view of an illustrative embodiment of a container for receiving and processing body fluids.

Referring now primarily to FIGS. 5-6, another illustrative embodiment of the container 304 for receiving and processing body fluids 330 is presented. The container 304 may be used as part of a medical treatment system, such as the system 100 of FIG. 1. The container 304 includes a container housing 326 having an interior space 328 for receiving the body fluids 330.

The container housing 326 has a housing 350 formed from a first material, such as rigid polymer, and formed with a plurality of apertures 352. The apertures 352 may take any shape, e.g., elongated slits, squares, triangles, but are shown as annular openings. A liquid-impermeable, vapor-permeable material 336 may be coupled to an interior portion of the housing 350 over the plurality of apertures 352. Alternatively, the liquid impermeable, vapor-permeable material 336 may be coupled to an exterior portion of the housing 350 over the plurality of apertures 352. A wicking member 337 is associated with the liquid-impermeable, vapor-permeable material 336 to enhance the transfer rate. The wicking member 337 may be coupled to or disposed proximate to the liquid-impermeable, vapor-permeable material 336. The liquid-impermeable, vapor-permeable material 336 may be welded, bonded, or coupled using any technique or device.

A plurality of windows 338 are formed having the liquid-impermeable, vapor-permeable material 336 separating the interior space 328 and an exterior. The windows 338 may be formed by forming a plurality of window apertures 335 and covering them with the liquid-impermeable, vapor-permeable material 336—a single piece or a plurality of pieces. The liquid-impermeable, vapor-permeable material 336 may be coupled to the container housing 126 using any known technique, including without limitation welding (e.g., ultrasonic or RF welding), bonding, adhesives, cements, or other coupling device. As suggested by arrows 340, a liquid in the body fluids 330—typically water—evaporates and egresses through the windows 338. The container 304 of the illustrative embodiment of FIGS. 5 and 6 provides structural strength from the housing 350 and provides surface area in the windows 338 for evaporation and transmission of the liquids from the body fluids 330.

The body fluids 330 enter the interior space 328 through a body fluids inlet 332. In this illustrative embodiment, a reduced-pressure source 322, which provides reduced pressure 323, is disposed in the interior space 328. For example, the reduced-pressure source 322 may be the piezoelectric pump 354. The reduced-pressure source 322 may exhaust its positive pressure through a vent 356. One or more electrical leads 358 may provide power and control to the reduced-pressure source 322. Because the reduced-pressure source 322 is a heat-generating vacuum pump or device, the reduced-pressure source 322 provides net thermal energy 325 into the interior space 328 and thereby helps to heat the body fluids 330. An increase in temperature of the body fluids 330 increases the evaporation rate. For this reason, other approaches to increasing the temperature of the body fluid or the liquid-impermeable, vapor-permeable member 336 may be used, such as applying the container to the patient's skin, creating an exothermic reaction within the container, using the sugar of the exudates to create power for a local electrical heater, or other techniques.

Figure 7:
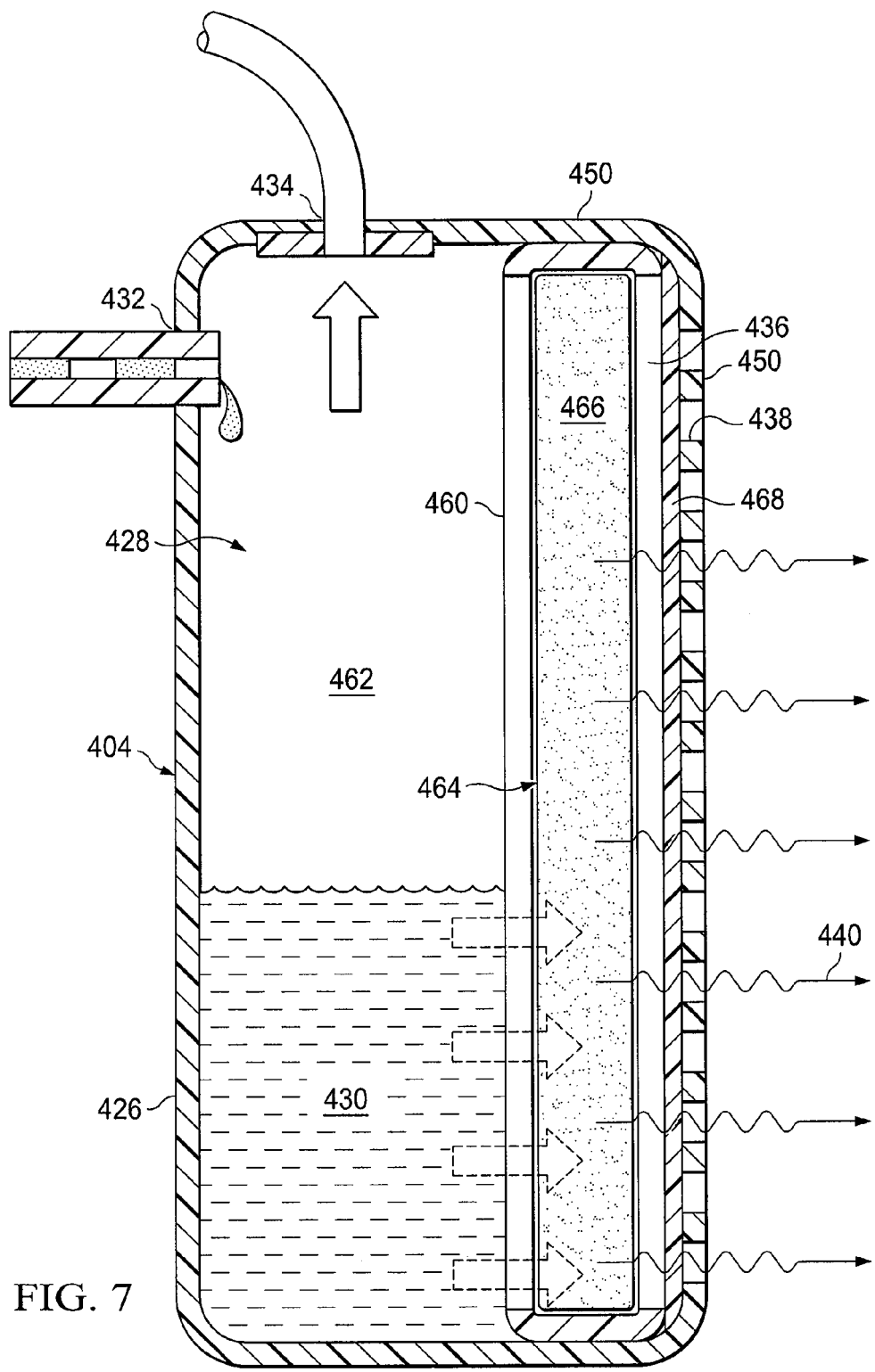
FIG. 7 is a schematic cross section of an illustrative embodiment of a container for receiving and processing body fluids.

Another illustrative embodiment involves first isolating certain liquids from other components of the body fluids using an osmotic pump. Thus, for example, referring primarily to FIG. 7, another illustrative embodiment of a container 404 for receiving and processing body fluids 430, which are primarily liquids, is presented that includes an osmotic membrane 460.

The container 404 includes a container housing 426 having an interior space 428 for receiving the body fluids 430. The interior space 428 has a wound fluid portion 462 and an osmotic fluid portion 464 separated by the osmotic membrane 460. The osmotic fluid portion 464 may have a salt-loaded wicking member 466. Water is pulled across the osmotic membrane 460 and into the osmotic fluid portion 464.

The osmotic fluid portion 464 is in fluid communication with the liquid-impermeable, vapor-permeable material 436. Thus, water in the osmotic fluid portion 464 encounters a liquid-impermeable, vapor-impermeable material 436 and evaporation and transmission occur as suggested by arrows 440. The vapor leaves through windows 438 in the container housing 426. As shown, an optional protective cover 468 may be disposed between the liquid-impermeable, vapor-impermeable material 436 and the housing frame 450.

A body fluid inlet 432 may be formed on the container housing 426. The body fluid inlet 432 is for receiving the body fluids 430 into the interior space 428 of the container housing 426 and in particular into the wound fluid portion 462. A reduced-pressure inlet 434 may be included in the container housing 426 to allow the introduction of reduced pressure into the interior space 428. Alternatively, a reduced-pressure source may be contained within the interior space 428.

Figure 8:
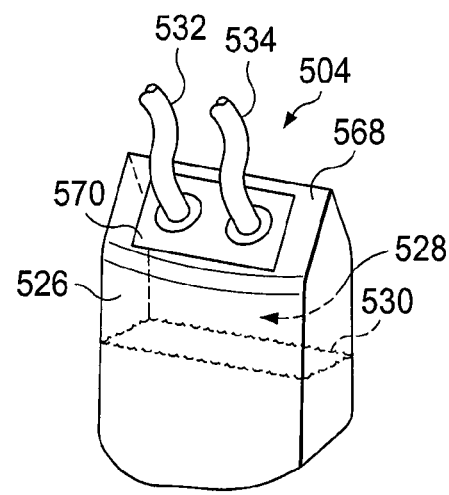
FIG. 8 is schematic perspective view of an illustrative embodiment of a container for receiving and processing body fluids.

Referring now primarily to FIG. 8, another illustrative embodiment of a container 504 for receiving and processing body fluids 530 is presented. The container 504 includes a container housing 526 in the form of a flexible pouch 568. The flexible pouch 568 may be contained within a rigid housing (not shown).

The flexible pouch 568 is substantially formed from a liquid-impermeable, vapor-permeable material. The container housing 526 has an interior space 528 for receiving the body fluids 530. An attachment plate 570 may be attached to the container housing 526. A body fluid inlet 532 and a reduced-pressure inlet 534 may be formed on the attachment plate 570. If a rigid housing is used to contain the flexible pouch 568, the body fluid inlet 532 and reduced-pressure inlet 534 would be coordinated with openings on the rigid housing. A foam spacer, internal polymer frame, or other spacer member (not shown) may be coupled to the body fluid inlet 532 and reduced-pressure inlet 534 (or otherwise associated with the interior space 528) to avoid a vacuum lock as the flexible pouch 568 collapses under the influence of reduced pressure.

Figure 9:
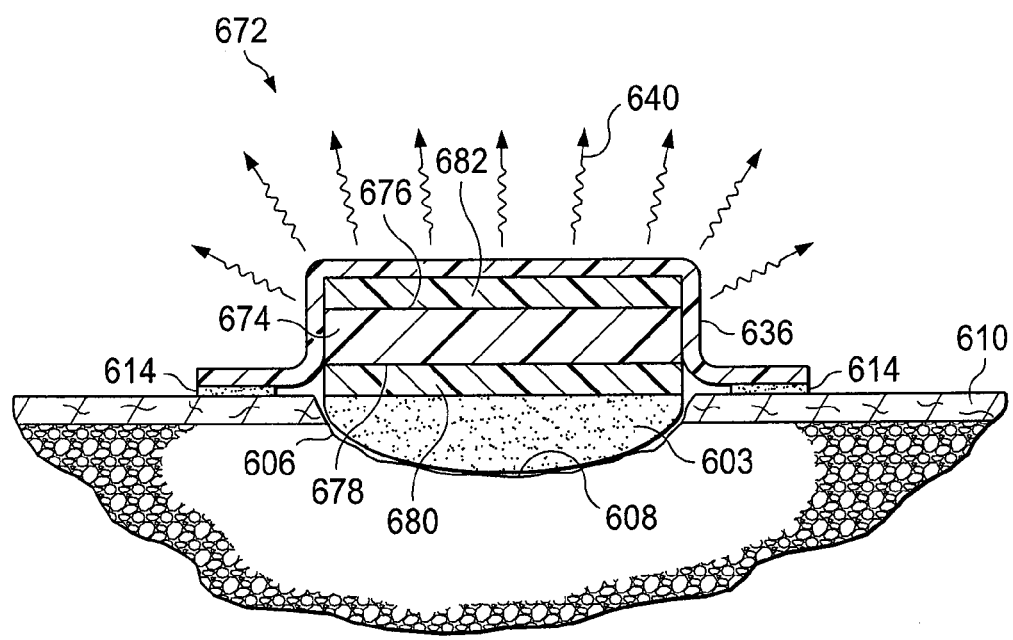
FIG. 9 is a schematic cross section of an illustrative embodiment of a wound dressing for treating a wound on a patient.

Referring now primarily to FIG. 9, an illustrative embodiment of a wound dressing 672 for treating a tissue site 606, such as a wound 608, on a patient is presented. The wound 608 may extend through the patient's epidermis 610. The wound dressing 672 may include a treatment manifold 603 that is placed proximate to the tissue site 606. An absorbent layer 674 is placed into fluid communication with the tissue site 606 to receive body fluids therefrom. The absorbent layer 674 has a first side 676 and a second, patient-facing side 678.

The wound dressing 672 may also include a first wicking layer 680 that may be disposed proximate to the second, patient-facing side 678 of the absorbent layer 674. The wound dressing 672 may also have a second wicking layer 682 that is disposed proximate to the first side 676 of the absorbent layer 674 and to a liquid-impermeable, vapor-permeable layer 636. The liquid-impermeable, vapor-permeable layer 636 covers the absorbent layer 674 and the tissue site 606 and functions as a covering or drape. The liquid-impermeable, vapor-permeable layer 636 may be held to the patient's epidermis 610 by an attachment device 614. Fewer layers may be included or more layers may be added and the order of the layers may be changed. A micropump (not shown) may be included below the liquid-impermeable, vapor-permeable layer 636 to provide reduced pressure.

Similar to other embodiments presented herein, the liquid-impermeable, vapor-permeable layer 636 is operable to allow liquids in the body fluids to evaporate and exit the liquid-impermeable, vapor-permeable layer 636 as suggested by arrows 640. In this way, the absorbent layer 674 is able to receive more body fluids over an elapsed time period than the absorbent layer 674 could retain otherwise.

In any of the embodiments herein, a flocculation agent could be added to the interior space of the container. Thus, for example, according to another illustrative embodiment, a body fluid in the form of a liquid from a tissue site is delivered through a reduced-pressure delivery conduit, e.g., the first reduced-pressure conduit 120 in FIG. 1, to a container, e.g., the container 104 in FIG. 1. In the container, evaporation is promoted as presented in the various embodiments herein, but in addition the body fluid is flocculated.

Flocculation is the process that causes fine particulates to clump together into floc. The floc often floats to the top of the liquid, settles to the bottom of the liquid, or is filtered from the liquid. The remaining liquid, or clarified liquid, is more pure. The clarified liquid may then be exposed to ion exchange materials (e.g., polymers with strong cations and anions) to remove the salts and produce a resultant clarified liquid.

In carrying out the flocculation process, the container may contain a separate portion on an interior of the container or elsewhere that contains a flocculation agent. The flocculation agent is introduced into a portion of the container holding the body fluid in order to cause flocculation. Alternatively, the flocculation agent may be supported on a filter or non-woven material. Any suitable flocculation agent may be used including the following: polyelectrolytes, aluminum sulphate, aluminum, iron, calcium or magnesium.

The resulting clarified fluid is exposed to a liquid-impermeable, vapor-permeable material, e.g., the liquid-impermeable, vapor-permeable material 136 in FIG. 1, and at least of the portion of the remaining liquid evaporates and egresses the liquid-impermeable, vapor-permeable material. Adding flocculation to a system, such as the system 100 of FIG. 1, may be an advantegous way of reducing fouling or potential fouling of the liquid-impermeable, vapor-permeable material. In addition, the clarified fluid may evaporate more effectively and egress the liquid-impermeable, vapor-permeable material.

Figure 10:
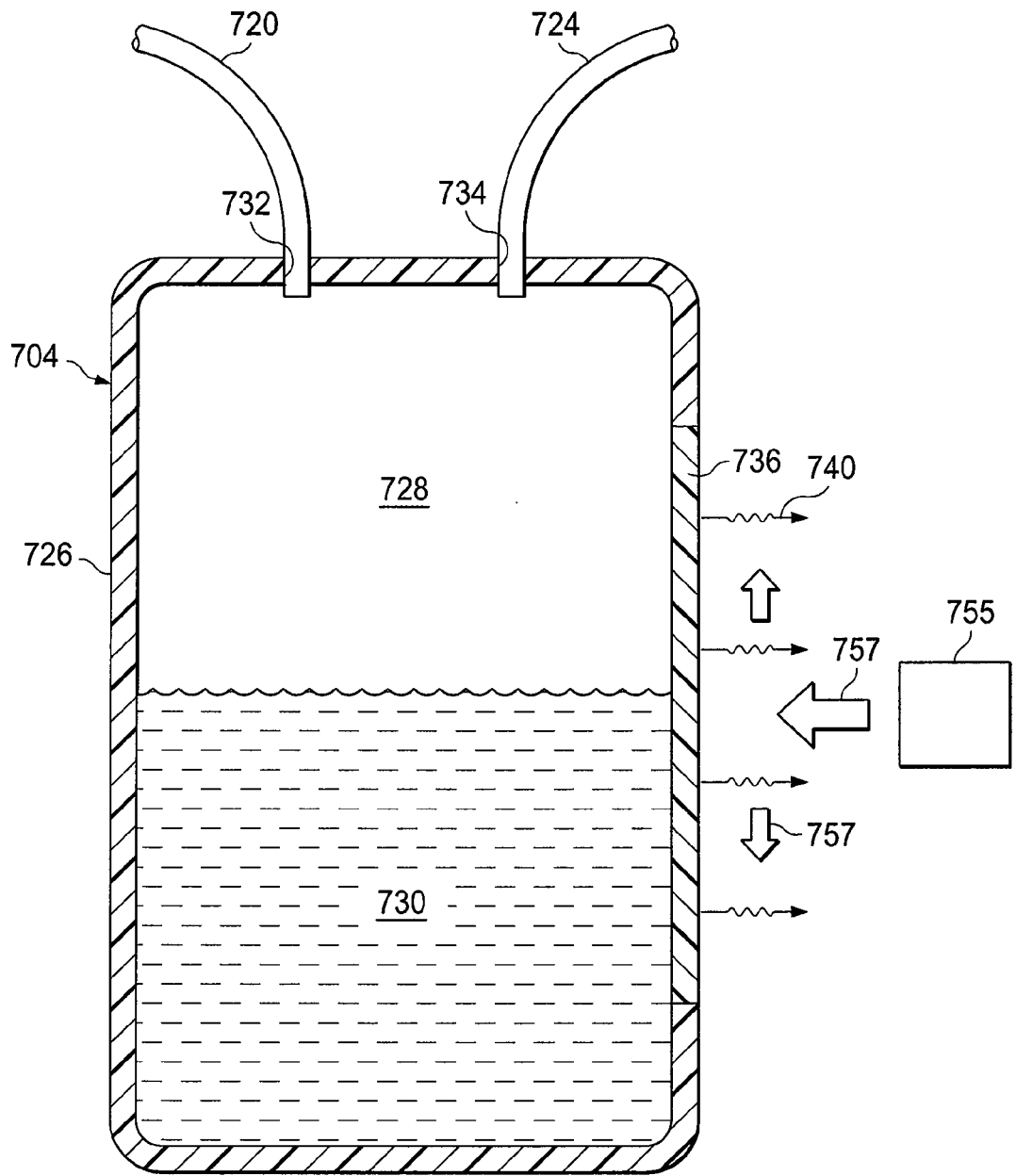
FIG. 10 is a schematic cross section of an illustrative embodiment of a container for receiving and processing body fluids.

Referring now primarily to FIG. 10, an illustrative embodiment of a container 704 for receiving and processing body fluids (primarily liquids) from a patient is presented. The container 704 is operable to process more liquids over time than the container 704 can physically retain at one time. The container 704 is analogous to previously presented containers, but a forced-air device 755 has been added to increase the rate of water vapor transport.

The container 704 includes a container housing 726 having an interior space 728 for receiving the body fluids 730. The container housing 726 has a fluid inlet, or a body fluid inlet 732, for receiving the body fluids 730 from a conduit 720. The container housing 726 has a reduced pressure inlet 734 for receiving reduced pressure from a conduit 724 from a reduced-pressure source (not shown). At least a portion of the container housing 726 comprises a liquid-impermeable, vapor-permeable material 736. The liquid-impermeable, vapor-permeable material 736 may form the whole container 104 or may form only a portion, e.g., a wall or window 138.

In this illustrative embodiment, evaporation and egress (see arrows 740) through the liquid-impermeable, vapor-permeable material 736 may be enhanced by forcing air 757 across an exterior of the liquid-impermeable, vapor-permeable material 736 with the forced-air device 755. The forced-air device 755 may be a fan that directs air across the liquid-impermeable, vapor-permeable material 736 or fan with baffles and ducts. The forced-air device 755 may be a fan-less device such as an electrostatic device for moving air or a piezoelectric pump with baffles that move air. The forced-air device 755 may also be a plurality of ducts or baffles and an intentional leak in the container 704 that allows reduced pressure to pull air through the ducts across the liquid-impermeable, vapor-permeable material 736 before entering the interior space 728. The movement of air across the liquid-impermeable, vapor-permeable material 736 increases the rate of water vapor transport. Without being limited by theory, the moisture gradient across the liquid-impermeable, vapor-permeable material 736 may pull water from the wound fluid 730.

Figure 11:
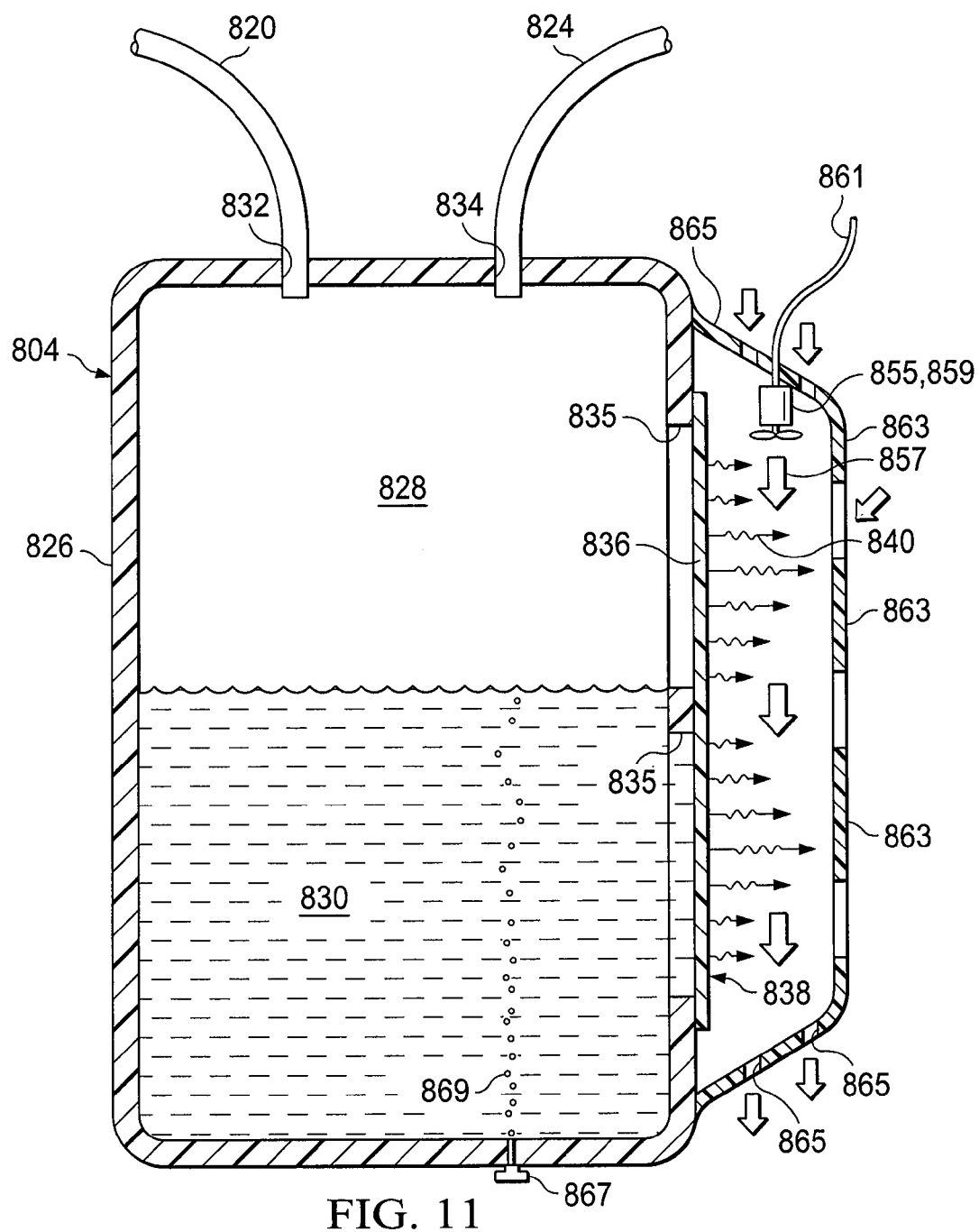
FIG. 11 is a schematic cross section of an illustrative embodiment of a container for receiving and processing body fluids.

Referring now primarily to FIG. 11, an illustrative embodiment of a container 804 for receiving and processing body fluids (primarily liquids) from a patient is presented. The container 804 is operable to process more liquids over time than the container 804 can physically retain at one time. The container 804 is analogous in most respects to the previously presented containers and particularly to container 704 of FIG. 10.

The container 804 has a container housing 826 forming an interior space 828. The interior space 828 receives body fluids 830 (primarily liquids) through a delivery conduit 820 that is fluidly coupled to body fluid inlet 832. Reduced pressure may be delivered from a reduced-pressure source through a delivery conduit 824 to a reduced-pressure inlet 834.

One or more windows 838 are formed on the container housing 826. The one or more windows 838 may be formed by forming one or more window apertures 835 and covering (on the interior, exterior, or a sill) the window aperture(s) 835 with a liquid-impermeable, vapor-permeable material 836. The liquid-impermeable, vapor-permeable material 836 may be coupled to the container housing 826 using any known technique, including without limitation welding (e.g., ultrasonic or RF welding), bonding, adhesives, cements, or other coupling device.

A forced-air device 855 is positioned to provide forced air along the liquid-impermeable, vapor-permeable material 836 to increase the rate of water vapor transport. In this illustrative embodiment, the forced-air device 855 is a fan 859. The forced-air device 855 may be powered by a battery or an external connection 861. A plurality of baffles walls 863 may be formed as part of or coupled to the container housing 826. The forced-air device 855 may be coupled to a baffle wall of the plurality of baffle walls 863. The baffle walls 863 may have a plurality of vent openings 865 for directing air flow. The forced-air device 855 causes air to impact or move across the liquid-impermeable, vapor-permeable material 836.

As with other embodiments herein, vaporization of the body fluids 830 may be enhanced by an interior-energy device that adds energy into the interior space 828. The interior-energy device may be a heating element or device for adding thermal energy, an agitator for moving the body fluids 830 against the window(s) 838, or a bubbler 867 to create bubbles 869 in the body fluids 830. The bubbler 867 may include a small pore size filter to prevent expelling pathogenic material. The bubbler 867 may have a water collection device associated with the bubbler 869 to contain and water or liquids that may egress the bubbler 867 as it operates. The water collection device may be a container under the bubbler 867.

In operation according to one illustrative embodiment, the container 804 is fluidly coupled by delivery conduit 820 to a source of body fluids. The container 804 is also coupled by conduit 824 to a reduced-pressure source. (In an alternative embodiment, the reduced-pressure source may be within the container 804). The reduced-pressure source is activated and body fluids 830 are delivered into the interior space 828. The forced-air device 855, e.g., fan 859, is activated and air 857 is forced to impact or move across the liquid-impermeable, vapor-permeable material 836 on window 838. The vapor egresses through the liquid-impermeable, vapor-permeable material 836 (see arrows 840) at an enhanced rate.

Figure 12:
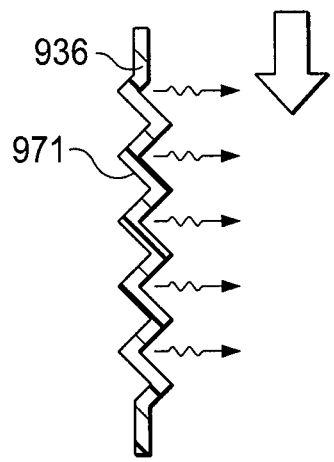
FIG. 12 is a schematic cross section of a portion of a liquid-impermeable, vapor-permeable material for use with a container or dressing for receiving and processing body fluids.
Figure 13:
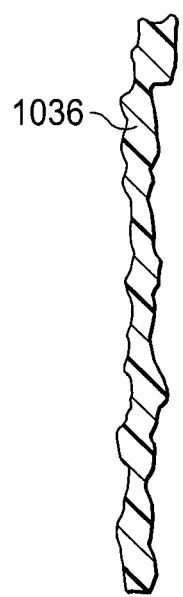
FIG. 13 is a schematic cross section of a portion of a liquid-impermeable, vapor-permeable material for use with a container or dressing for receiving and processing body fluids.
Figure 14:
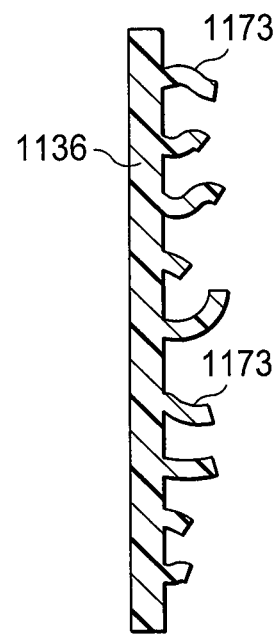
FIG. 14 is a schematic cross section of a portion of a liquid-impermeable, vapor-permeable material for use with a container or dressing for receiving and processing body fluids.

Other features may be included as an aspect of the containers 104, 204, 304, 404, 50.4, 604, 704, and 804 to enhance evaporation. For example, referring now to FIG. 12, a liquid-impermeable, vapor-permeable material 936 may be used that has corrugations 971. The liquid-impermeable, vapor-permeable material 936 may be used any of the embodiments herein as the liquid-impermeable, vapor-permeable material 136, 236, 336, 436, 536, 636, 736, 836, 1236, or 1336. As air 957 is forced across the liquid-impermeable, vapor-permeable material 936 more surface area may interact with the air. In addition or alternatively, a textured liquid-impermeable, vapor-permeable material 1036 may be used as shown in FIG. 13. As shown in FIG. 14, the liquid-impermeable, vapor-permeable material 1136 may include flocking 1173 or fine fibers that provide additional area on an exterior portion of the liquid-impermeable, vapor-permeable material 1136. In addition to the flock 1173 or fine fibers, other porous wicks may be employed such as hydrophylic, open-celled foam (e.g., polyurethane, polyvinyl alcohol, cellulose); or sintered polymers (e.g., polyolefin, polyamide, polyester, acrylic) surface treated to be hydrophylic.

Figure 15:
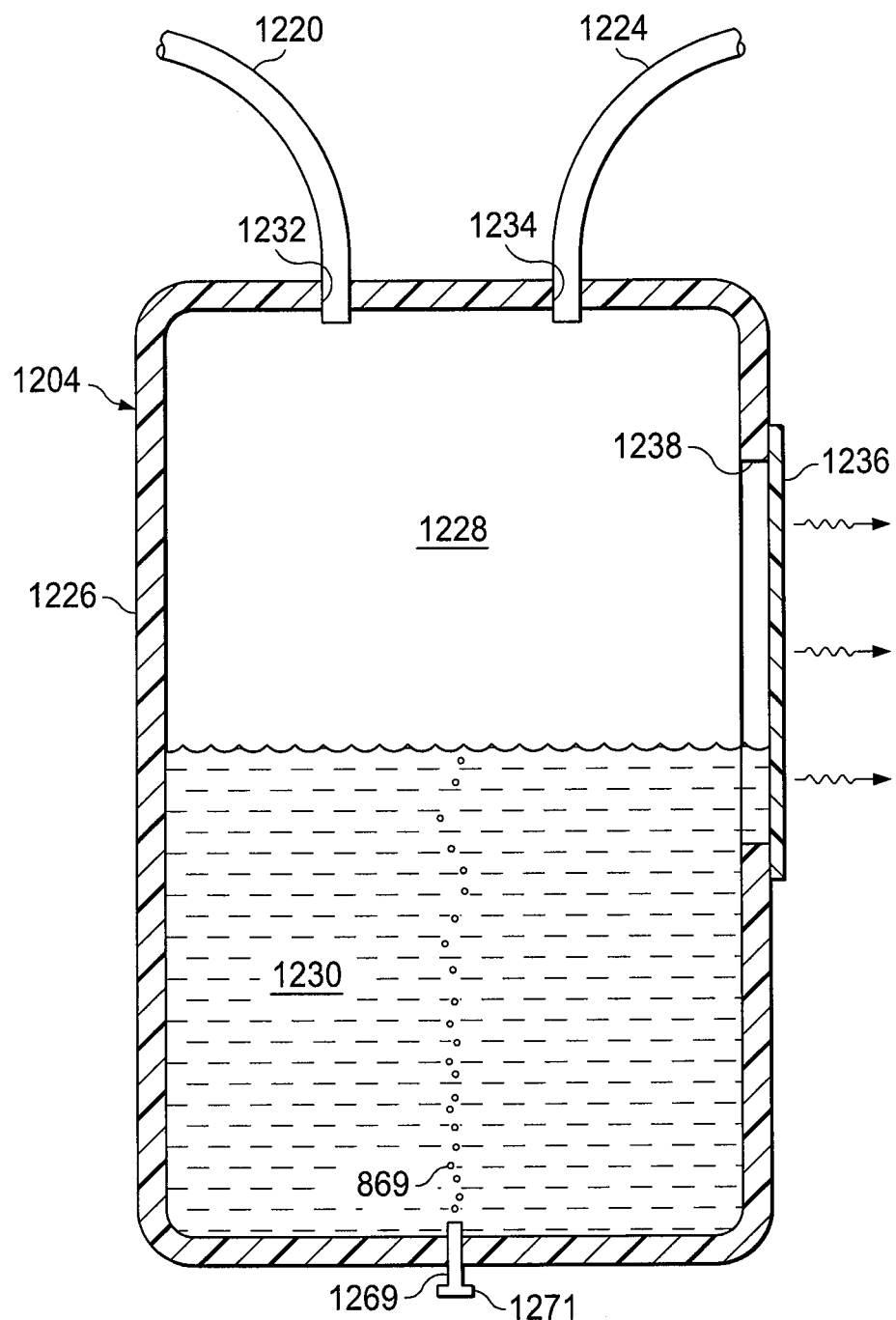
FIG. 15 is a schematic cross section of an illustrative embodiment of a container for receiving and processing body fluids.

Referring now primarily to FIG. 15, an illustrative embodiment of a container 1204 for receiving and processing body fluids (primarily liquids) from a patient is presented. The container 1204 is operable to process more liquids over time than the container 1204 can physically retain at one time. The container 1204 is analogous to previously presented containers, but the interior-energy device is different. The interior-energy device is a conduit 1269 and valve 1271 that have been added to increase energy within an interior space 1228. The interior-energy device is a conduit 1269 moves the liquids within the interior space 1228.

The container 1204 includes a container housing 1226 having the interior space 1228 for receiving the body fluids 1230. The container housing 1226 has a fluid inlet 1232 for receiving the body fluids 1230 from a conduit 1220. The container housing 1226 has a reduced pressure inlet 1234 for receiving reduced pressure from a conduit 1224 from a reduced-pressure source (not shown). At least a portion of the container housing 1226 comprises a liquid-impermeable, vapor-permeable material 1236. The liquid-impermeable, vapor-permeable material 1236 may form the whole container 1204 or may form only a portion, e.g., a wall or window 1238. The liquid-impermeable, vapor-permeable material 1236 is shown coupled on an exterior of the container 1204, but could also be on the interior or flush with the container 1204.

The valve 1271 and conduit 1269 provide energy in the form of bubbles into the interior space 1228. The valve 1271 provides control of the air entering the sealed space 1228. The valve may restrict or close off fluid flow in the conduit 1269 and thereby control the flow therein. The valve 1271 may be manually operated or include solenoid or other control device that is coupled to a controller. The flow of air through conduit 1269 may be controlled and may be constant or intermittent.

Figure 16:
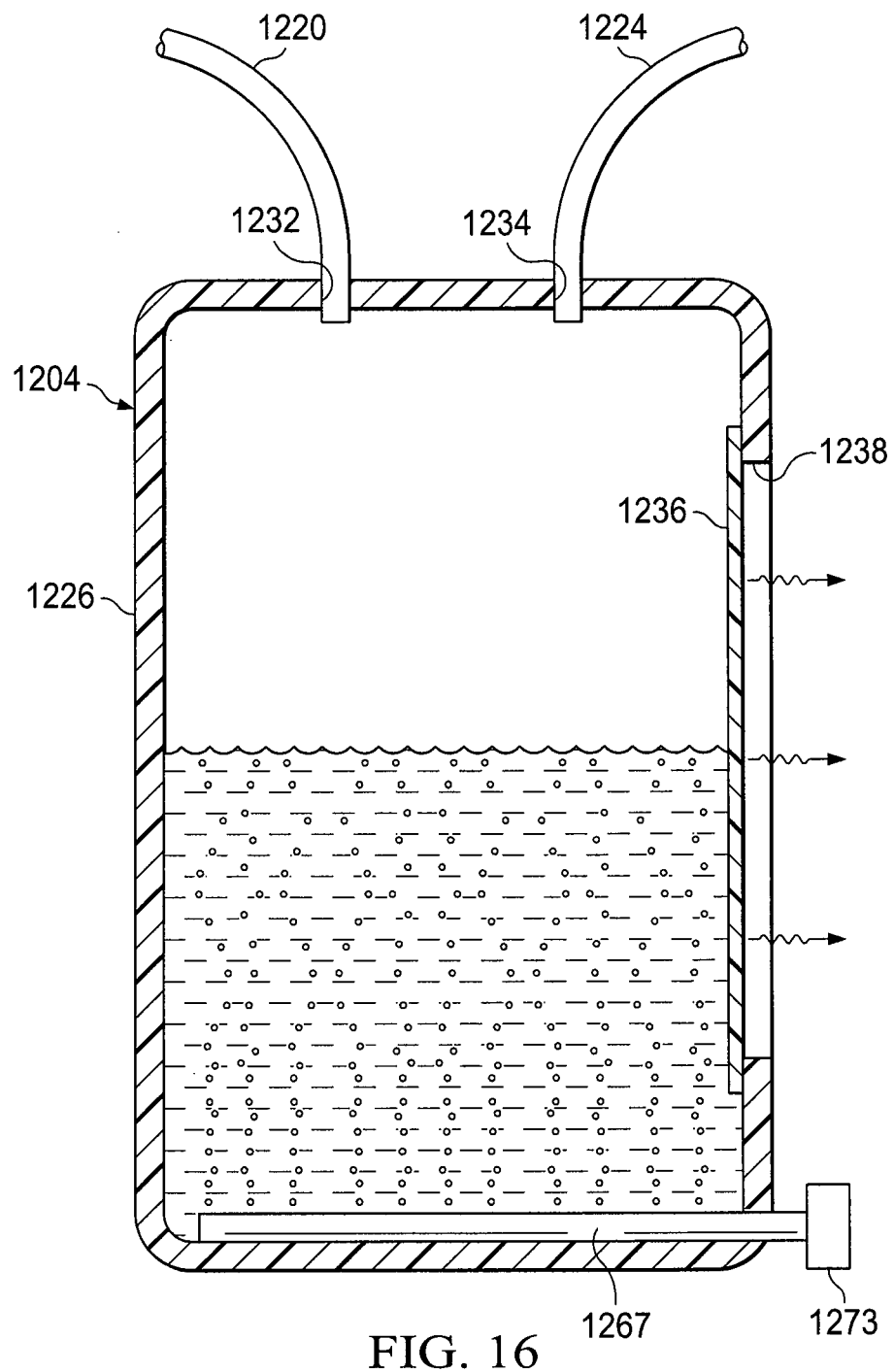
FIG. 16 is a schematic cross section of an illustrative embodiment of a container for receiving and processing body fluids.

Referring now primarily to FIG. 16, another illustrative embodiment of a container 1204 for receiving and processing body fluids (primarily liquids) from a patient is presented. The container is analogous to the container of FIG. 15 and the same reference numerals are used. The main difference between the embodiments of FIGS. 15 and 16 is that the conduit 1269 and valve 1271 have been replaced with an interior-energy device in the form of a longitudinal bubbler 1267. The longitudinal bubbler 1267 is fluidly coupled to the valve 1273.

The longitudinal bubbler 1267 delivers additional energy in the form of bubbles into the interior space 1228. The longitudinal bubbler 1267 may be any device that distributes bubbles within the interior space 1228. For example, the longitudinal bubbler 1267 may be a porous, gas-permeable, water-impermeable, hydrophobic member, such as a sintered polymer membrane, PTFE, or other suitable material. As with valve 1271, valve 1273 may deliver air continuously or intermittently.

Figure 17:
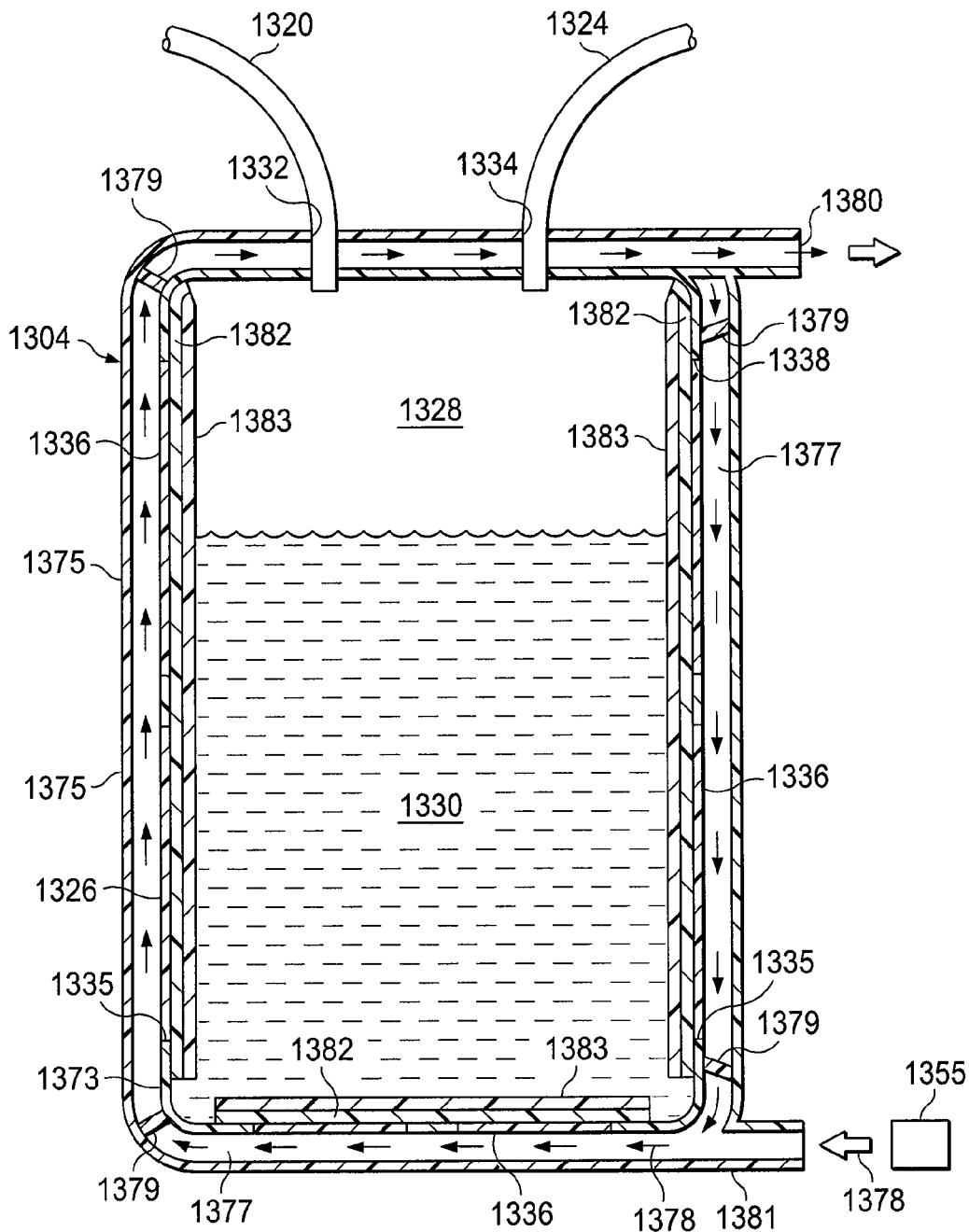
FIG. 17 is a schematic cross section of an illustrative embodiment of a container for receiving and processing body fluids.

Referring now primarily to FIG. 17, an illustrative embodiment of a container 1304 for receiving and processing body fluids (primarily liquids) from a patient is presented. The container 1304 is operable to process more liquids over time than the container 1304 can physically retain at one time. The container 1304 is analogous in many respects to the previously-presented containers.

The container 1304 has a container housing 1326 forming an interior space 1328. The interior space 1328 receives body fluids 1330 (primarily liquids) through a delivery conduit 1320 that is fluidly coupled to a body fluid inlet 1332. Reduced pressure may be delivered from a reduced-pressure source through a delivery conduit 1324 to a reduced-pressure inlet 1334.

The container housing 1326 has an inner wall 1373 and an outer wall 1375, or shell. The space between the inner wall 1373 and outer wall 1375 forms a passageway 1377. One or more spaced support members 1379 may be used to hold the inner wall 1373 and outer wall 1375 in relative position to one another. Alternatively or in addition to spaced support members 1379, the space between the inner wall 1373 and the outer wall 1375, i.e., the passageway 1377, may be filled with a porous, continuous or substantially continuous support.

One or more windows 1338 are formed on the container housing 1326. The one or more windows 1338 may be formed by forming one or more window apertures 1335 and covering the window aperture(s) 1335 with a liquid-impermeable, vapor-permeable material 1336. The liquid-impermeable, vapor-permeable material 1336 may be coupled to the container housing 826 using any known technique, including without limitation welding (e.g., ultrasonic or RF welding), bonding, adhesives, cements, or other coupling device. As with the other embodiments, the liquid-impermeable, vapor-permeable material 1336 may be attached within the window aperture(s) 1335 as shown or may be on an interior or exterior of the container housing 1326.

A passageway inlet 1381 is formed in the container housing 1326 to allow fluid access to the passageway 1377. A forced-air device 1355 is positioned to deliver forced air into the passageway inlet 1381. The forced air 1378 moves through the passageway 1377 and across the liquid-impermeable, vapor-permeable material 1336. A passageway outlet 1380 is formed in the container housing 1326 to allow the forced air 1378 and vapor to exit the passageway 1377. In another embodiment, the forced-air device 1355 may be positioned within the passageway 1377.

A wicking layer 1382 may be coupled to an interior of the inner wall 1373. The wicking layer 1382 spreads the liquids in the interior space 1328 around and causes more liquid contact with the liquid-impermeable, vapor-permeable material 1336. The wicking layer 1382 may cover only the liquid-impermeable, vapor-permeable material 1336 or may cover the entire interior of the inner wall 1373. A filter layer 1383 may be coupled to an interior side of the wicking layer 1382. The filter layer 1383 may be used to reduce the amount of fluid-borne particulate reaching and possibly fouling the wicking layer 1382.

With respect generally to forced-air devices 755, 855, 1355, which may added to any of the embodiments herein, the forced air flow may be intermittent (e.g., pulsed) or continuous. Moreover, the air flow may be reversed to flow in the opposite direction. A humidity or moisture sensor may be placed downstream of the liquid-impermeable, vapor-permeable material involved. The humidity or moisture sensor may be coupled to a controller or otherwise configured to switch off the forced-air device 755, 855, 1355 when moisture levels detected are below a minimum threshold over a time interval. In another embodiment, a humidity or moisture sensor may be placed inside the interior space of the container and the forced-air device only activated when moisture is detected in the interior space.

Although the present invention and its advantages have been disclosed in the context of certain illustrative, non-limiting embodiments, it should be understood that various changes, substitutions, permutations, and alterations can be made without departing from the scope of the invention as defined by the appended claims. As an non-limiting example, it should be understood that the osmotic membrane 460 of FIG. 7 may be included in the interior space 828 of the container 804 of FIG. 11. As another non-limiting example, the waffle pockets 246 of FIG. 4 may be added to the other embodiments herein. As another non-limiting example, the protective cover 468 of FIG. 7 could be added to other embodiments herein. As yet another non-limiting example, the bubbler 867 or forced-air device 855 of FIG. 11 could be added to any of the embodiments herein.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further embodiments having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A system for treating a tissue site with reduced pressure, the system comprising:
   a treatment manifold for placing proximate to the tissue site;

a sealing member for forming a fluid seal over the treatment manifold to form a sealed treatment space;
a reduced-pressure source for providing reduced pressure; and
a container fluidly coupled to the reduced-pressure source and the sealed treatment space;
wherein the container comprises:
an interior space;
a fluid inlet fluidly coupled to the sealed treatment space and the interior space;
a reduced-pressure inlet fluidly coupled to the reduced-pressure source and the interior space; and
a window having a hydrophilic polymer adapted to allow water vapor to egress from the interior space separately from the reduced-pressure inlet while retaining liquids and maintaining reduced pressure.

2. The system of claim 1, further comprising a forced-air device associated with an exterior of the hydrophilic polymer.

3. The system of claim 2, wherein the forced-air device comprises one of the following: a fan, an electrostatic device, and a piezoelectric pump.

4. The system of claim 1, further comprising an interior-energy device for adding energy into the interior space of the container.

5. The system of claim 1, wherein the container further comprises a container frame and a plurality of baffles forming a plurality of waffle pockets and wherein the waffle pockets are covered by the hydrophilic polymer.

6. The system of claim 1, wherein the interior space has a wound fluid portion and an osmotic fluid portion separated by an osmotic membrane; and wherein the osmotic fluid portion is in fluid communication with the hydrophilic polymer.

7. The system of claim 1, wherein the container further comprises a flexible pouch formed substantially from the hydrophilic polymer.

8. The system of claim 1, further comprising a heating element disposed within the interior space.

9. The system of claim 1, wherein the interior space has a first volume ($V_c$) and wherein for an elapsed treatment time t, the container is operable to process a second volume ($V_f$) of fluids, wherein $V_f > 110\% V_c$.

10. The system of claim 1, further comprising a flocculating agent associated with the interior space.

11. The system of claim 1, wherein the hydrophilic polymer is substantially impervious to nitrogen and oxygen.

12. A container for receiving and processing body fluids, the container comprising:
an interior space;
a body fluid inlet fluidly coupled to the interior space;
a reduced-pressure inlet fluidly coupled to the interior space; and
a window having a hydrophilic polymer adapted to allow water vapor to egress from the interior space separately from the reduced-pressure inlet while retaining liquids and maintaining reduced pressure.

13. The container of claim 12, further comprising a forced-air device associated with an exterior of the hydrophilic polymer.

14. The container of claim 13, wherein the forced-air device comprises one of the following: a fan, an electrostatic device, and a piezoelectric pump.

15. The container of claim 12, wherein the hydrophilic polymer is corrugated.

16. The container of claim 12, further comprising an interior-energy device for adding energy into the interior space of the container.

17. The container of claim 12, wherein the container housing comprises a container frame and a plurality of baffles forming a plurality of waffle pockets and wherein the waffle pockets are covered by the hydrophilic polymer.

18. The container of claim 12, wherein the interior space has a wound fluid portion and an osmotic fluid portion separated by an osmotic membrane; and wherein the osmotic fluid portion is in fluid communication with the hydrophilic polymer.

19. The container of claim 12, wherein the container housing comprises a flexible pouch formed substantially from the hydrophilic polymer.

20. The container of claim 12, further comprising a heating element disposed within the interior space.

21. The container of claim 12, further comprising a heat-generating, reduced-pressure source, and wherein the heat-generating, reduced-pressure source is thermally coupled to the interior space.

22. The container of claim 12, wherein the interior space has a first volume ($V_c$) and wherein for an elapsed treatment time t, the container is operable to process a second volume ($V_f$) of the body fluids, wherein $V_f > 110\% V_c$.

23. The container of claim 12, further comprising a wicking layer coupled to an interior side of the hydrophilic polymer.

24. The container of claim 12, wherein a portion of the container contains a flocculation agent.

25. A method for processing body fluids from a patient, the method comprising:
causing the body fluids to enter into a container, wherein the container comprises:
an interior space;
a body fluid inlet fluidly coupled to the interior space;
a reduced-pressure inlet fluidly coupled to the interior space; and
a window having a hydrophilic polymer adapted to allow water vapor to egress from the interior separately from the reduced-pressure inlet while retaining liquids and maintaining reduced pressure; and
evaporating and removing at least a portion of the water from the body fluids using the hydrophilic polymer.

* * * * *